United States Patent
Erickson et al.

(10) Patent No.: US 8,425,573 B2
(45) Date of Patent: Apr. 23, 2013

(54) METHOD AND SYSTEM FOR ATTACHING A PLATE TO A BONE

(75) Inventors: Paul Lawrence Erickson, Eastlake, OH (US); Isador H. Lieberman, Ft. Lauderdale, FL (US); Stephen Edward Keverline, Mentor, OH (US)

(73) Assignees: The Cleveland Clinic Foundation, Cleveland, OH (US); Merlot Orthopedix Inc., Mentor, OH (US)

( * ) Notice: Subject to any disclaimer, the term of this patent is extended or adjusted under 35 U.S.C. 154(b) by 427 days.

(21) Appl. No.: 12/603,631

(22) Filed: Oct. 22, 2009

(65) Prior Publication Data

US 2010/0106196 A1 Apr. 29, 2010

Related U.S. Application Data

(60) Provisional application No. 61/108,280, filed on Oct. 24, 2008.

(51) Int. Cl.
*A61B 17/88* (2006.01)

(52) U.S. Cl.
USPC .................. 606/281; 606/86 B; 606/104

(58) Field of Classification Search .................. 606/281, 606/286, 96, 99, 86 B, 104
See application file for complete search history.

(56) References Cited

U.S. PATENT DOCUMENTS

| | | | | |
|---|---|---|---|---|
| 2,248,054 A * | 7/1941 | Becker | | 81/457 |
| 2,318,152 A * | 5/1943 | Gelardin | | 401/78 |
| 2,494,229 A * | 1/1950 | Collison | | 606/916 |
| 2,623,231 A * | 12/1952 | Gutenstein | | 401/116 |
| 4,755,092 A * | 7/1988 | Yaniv | | 411/554 |
| 5,364,399 A | 11/1994 | Lowery et al. | | |
| 5,423,826 A | 6/1995 | Coates et al. | | |
| 5,429,641 A | 7/1995 | Gotfried | | |
| 5,489,307 A | 2/1996 | Kuslich et al. | | |
| 5,569,264 A * | 10/1996 | Tamminmaki et al. | | 606/104 |
| 5,643,274 A * | 7/1997 | Sander et al. | | 606/104 |
| 5,680,954 A * | 10/1997 | Arnold et al. | | 220/300 |
| 5,722,105 A * | 3/1998 | Thomasson | | 15/120.2 |
| 5,755,721 A | 5/1998 | Hearn | | |
| 5,921,456 A | 7/1999 | Kirsch et al. | | |
| 6,139,549 A * | 10/2000 | Keller | | 606/86 A |
| 6,251,112 B1 | 6/2001 | Jackson | | |
| 6,299,616 B1 * | 10/2001 | Beger | | 606/86 R |
| 6,379,364 B1 | 4/2002 | Brace et al. | | |
| 6,436,100 B1 | 8/2002 | Berger | | |
| 6,565,571 B1 | 5/2003 | Jackowski et al. | | |
| 6,702,817 B2 | 3/2004 | Beger et al. | | |
| RE38,684 E | 1/2005 | Cesarone | | |

(Continued)

*Primary Examiner* — Kevin T Truong
*Assistant Examiner* — Zade Coley
(74) *Attorney, Agent, or Firm* — Tarolli, Sundheim, Covell & Tummino LLP

(57) ABSTRACT

A guide tool having a through bore and at least one distal locating feature is provided. The distal locating feature of the guide tool is placed into a predetermined relationship with the plate. A fastener is engaged with a distal end of a driver shaft of a fastener driver. The fastener driver has a driver orientation means associated with the driver shaft. The fastener is inserted into the through bore of the guide tool with the fastener driver. The driver orientation means is mated with a guide orientation means located in the through bore of the guide tool. At least a portion of the fastener is inserted through the fastener hole. The fastener is secured into the bone through actuation of the fastener driver. The fastener driver is withdrawn from the guide tool, which is withdrawn from the plate.

1 Claim, 21 Drawing Sheets

U.S. PATENT DOCUMENTS

| | | |
|---|---|---|
| 6,875,213 B2 | 4/2005 | Michelson |
| 6,923,814 B1 * | 8/2005 | Hildebrand et al. ............ 606/99 |
| 6,932,822 B2 | 8/2005 | Oribe et al. |
| 7,137,985 B2 | 11/2006 | Jahng |
| 7,166,111 B2 * | 1/2007 | Kolb et al. .................... 606/96 |
| 7,258,694 B1 * | 8/2007 | Choi et al. ................... 606/184 |
| 7,278,997 B1 | 10/2007 | Mueller et al. |
| 7,297,166 B2 | 11/2007 | Dwyer et al. |
| 7,666,189 B2 * | 2/2010 | Gerber et al. ................ 606/104 |
| 2002/0082606 A1 * | 6/2002 | Suddaby ......................... 606/96 |
| 2002/0151899 A1 * | 10/2002 | Bailey et al. ................... 606/69 |
| 2002/0183138 A1 * | 12/2002 | Malcolm ....................... 473/386 |
| 2003/0023246 A1 * | 1/2003 | Gotfried ....................... 606/104 |
| 2003/0153916 A1 | 8/2003 | Michelson |
| 2004/0092947 A1 * | 5/2004 | Foley ............................. 606/96 |
| 2004/0093971 A1 * | 5/2004 | Fujibayashi ................. 74/89.42 |
| 2005/0015093 A1 * | 1/2005 | Suh et al. ........................ 606/96 |
| 2005/0038444 A1 * | 2/2005 | Binder et al. .................. 606/96 |
| 2005/0149053 A1 | 7/2005 | Varieur et al. |
| 2005/0228398 A1 * | 10/2005 | Rathbun et al. ................ 606/96 |
| 2005/0251137 A1 * | 11/2005 | Ball ............................... 606/61 |
| 2006/0155298 A1 * | 7/2006 | Mueller et al. ............... 606/104 |
| 2006/0293693 A1 | 12/2006 | Farr et al. |
| 2007/0213726 A1 * | 9/2007 | McGarity et al. .............. 606/69 |
| 2007/0260261 A1 | 11/2007 | Runco et al. |
| 2007/0265499 A1 * | 11/2007 | Wood et al. ................... 600/137 |
| 2008/0097444 A1 * | 4/2008 | Erickson et al. ............... 606/69 |
| 2009/0036933 A1 * | 2/2009 | Dube et al. ................... 606/282 |

* cited by examiner

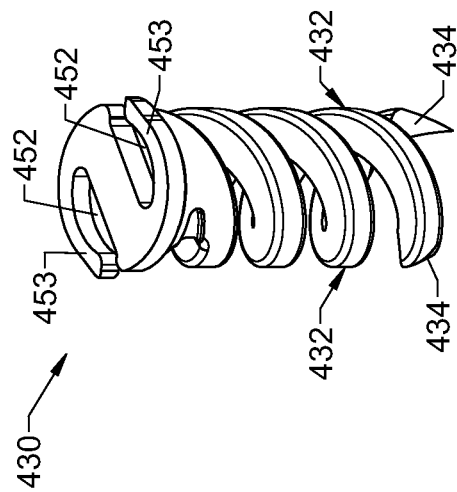
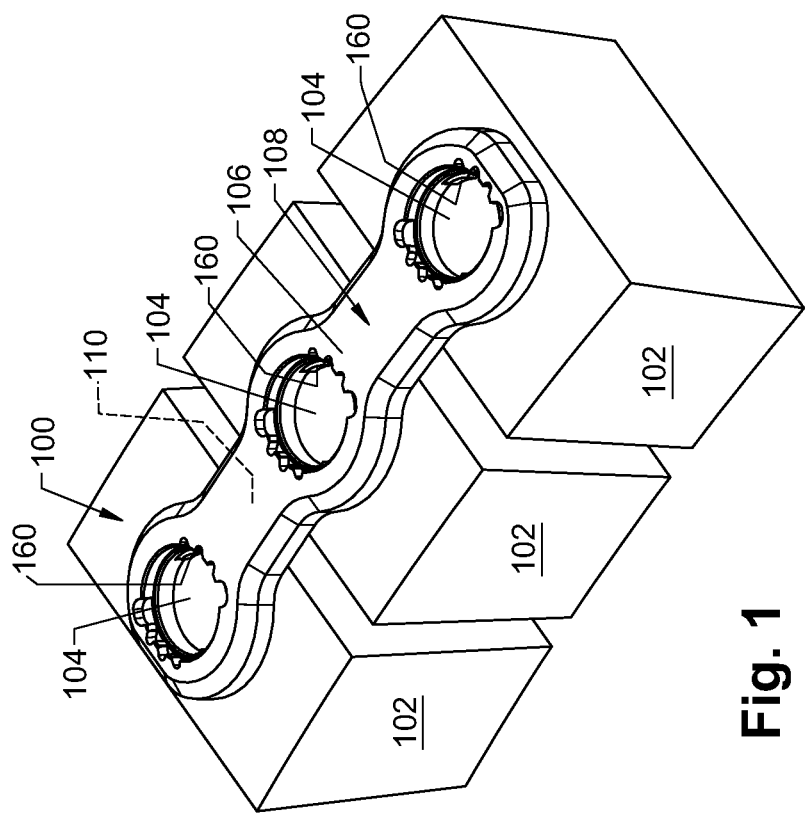

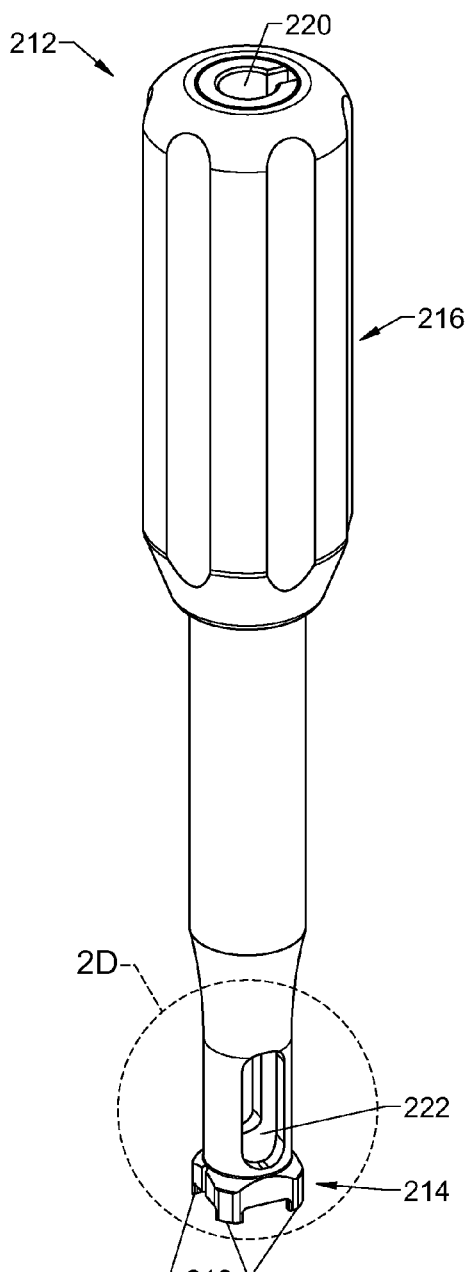
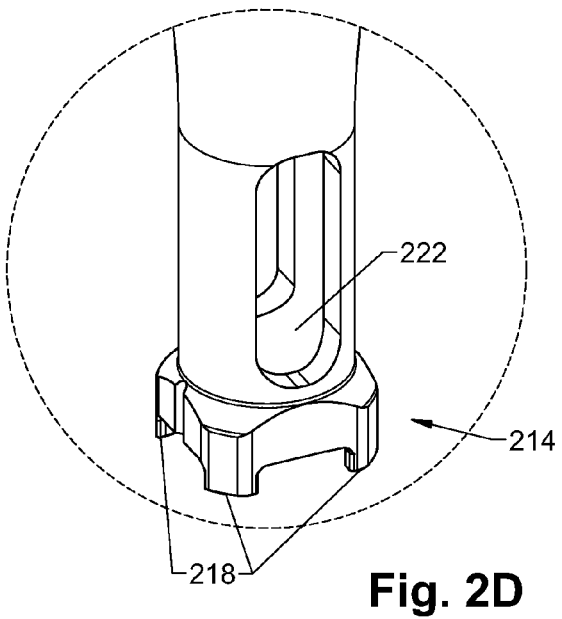
Fig. 2C
Fig. 2D

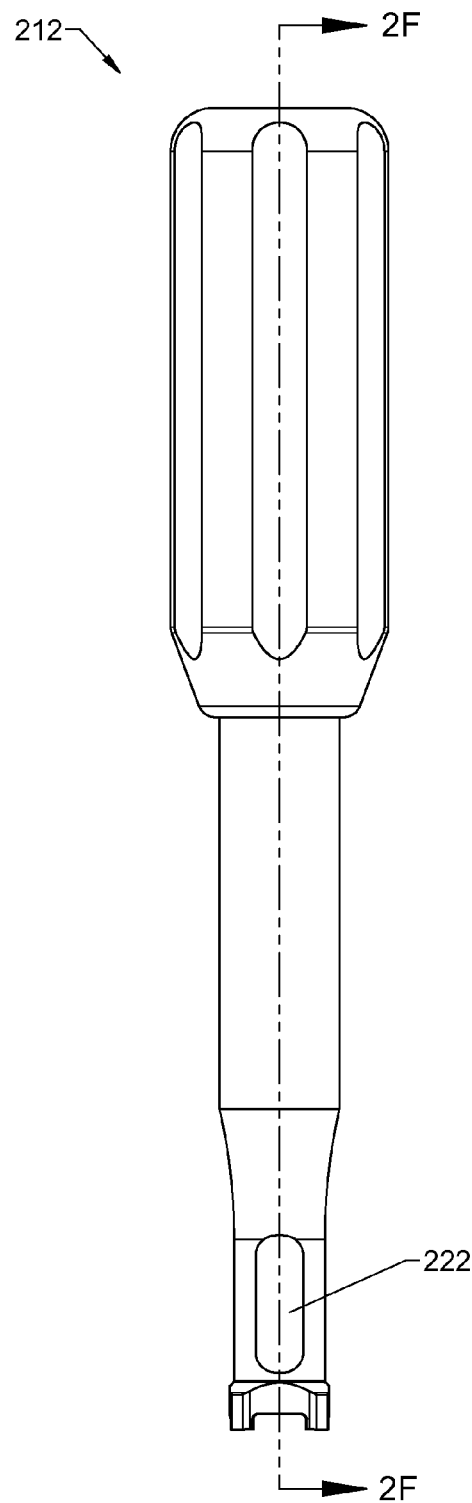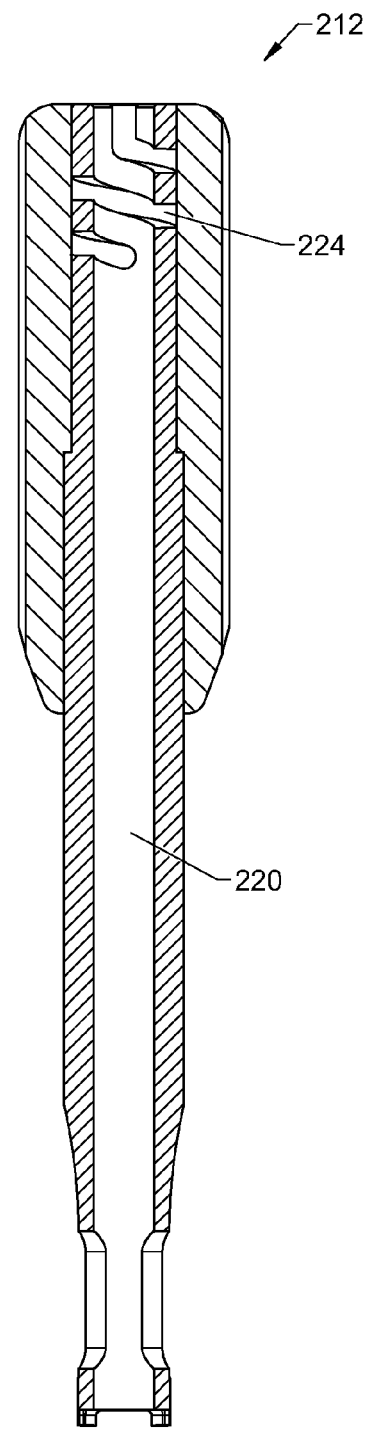
Fig. 2E
Fig. 2F

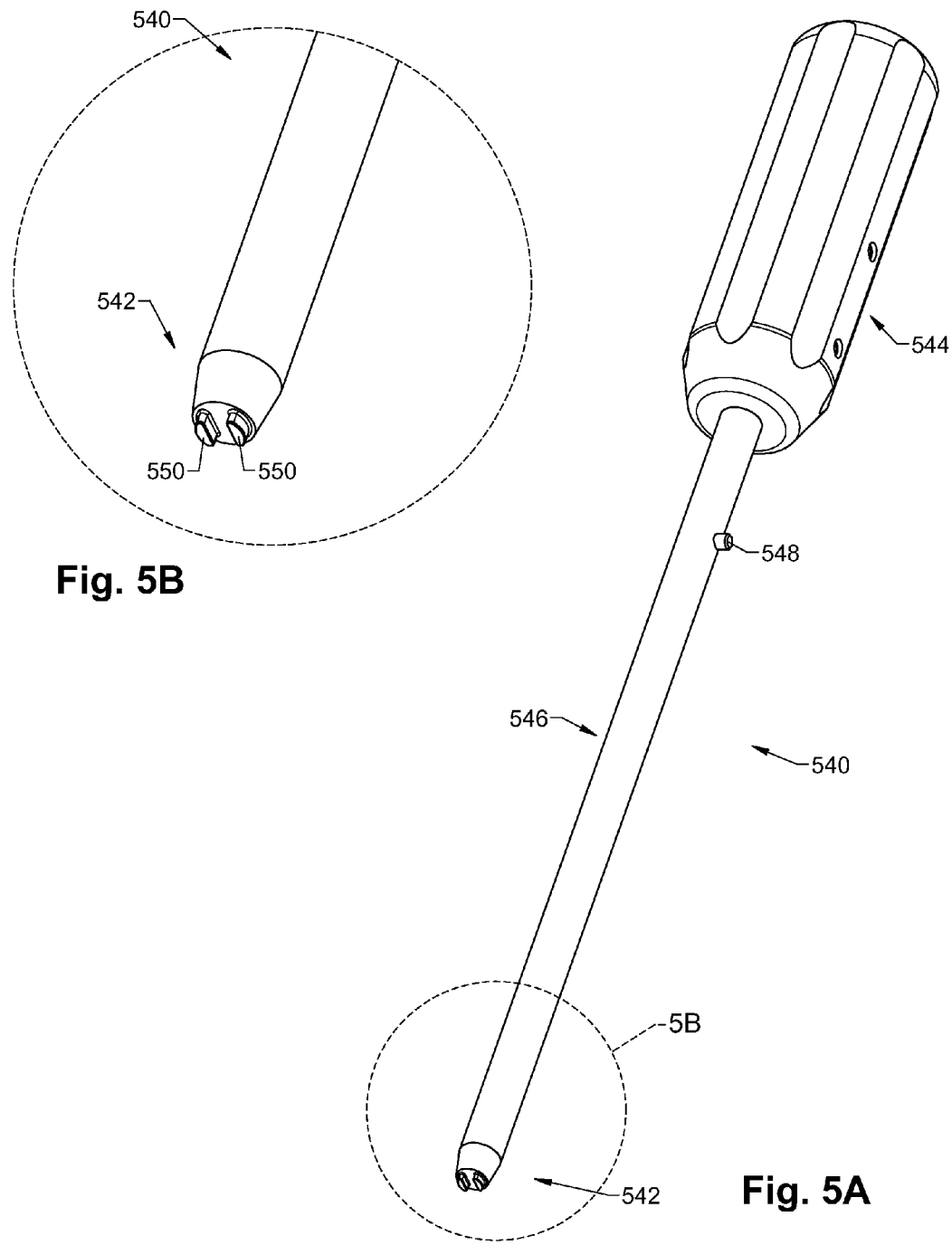

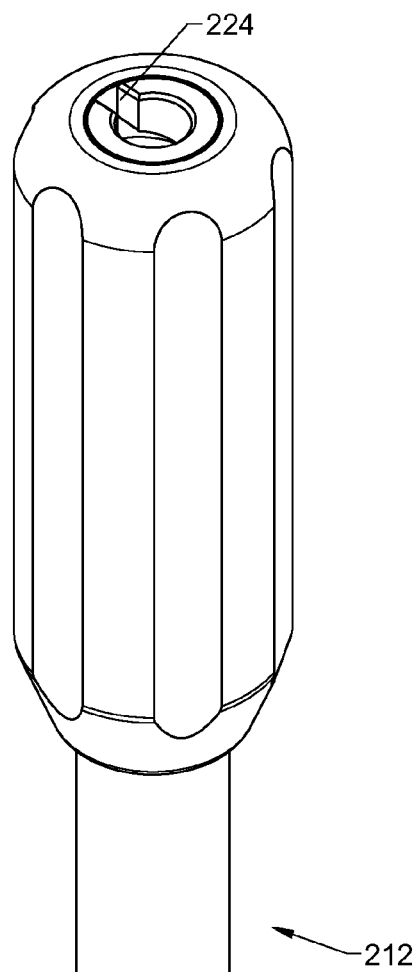
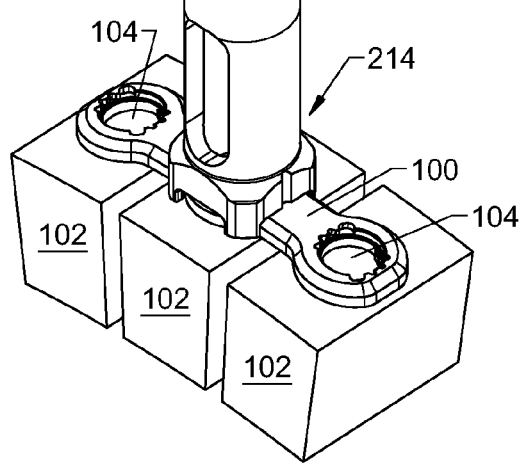
Fig. 6

METHOD AND SYSTEM FOR ATTACHING A PLATE TO A BONE

RELATED APPLICATION

This application claims priority from U.S. Provisional Application No. 61/108,280, filed 24 Oct. 2008, the subject matter of which is incorporated herein by reference.

TECHNICAL FIELD

The present invention relates to a method and system for attaching a plate to a bone and, more particularly, to a method and system for manipulating and securing a plate to a bone with a plurality of installation tools.

BACKGROUND OF THE INVENTION

In modern medicine, it is common to use one or more fixation plates for treatment of spinal disorders or for fusion of vertebrae. While early procedures using fixation plates were at the lower lumbar levels, spinal fixation plates have relatively recently found applications in the instrumentation of the cervical spine. Successful spinal instrumentation in this region is particularly difficult given the known problems of safely accessing the instrumentation site.

The upper cervical spine can be approached either anteriorly or posteriorly, depending upon the spinal disorder to be treated. Complications associated with access procedures can be devastating, such as injury to the brain stem, spinal cord, and/or vertebral arteries. In addition, a lengthy access procedure can contribute to other surgical complications, such as anesthetic-related issues or surgeon fatigue.

In addition to the normal complications associated with the mere exposure and fusion of the cervical spine, implantation of a spinal fixation plate adds to the degree of risk and complication. Most users place the fixation plate over the vertebral levels to be instrumented and use the plate as a drill guide for drilling and tapping the bone in preparation for receiving a fixation screw. Several known systems and procedures provide for a soft tissue protector in the form of an elongated sleeve which is intended to surround the drill and minimize damage to the surrounding muscle and other tissues.

There is a need for a cervical plating system which minimizes the intrusion into the patient and reduces trauma to the surrounding soft tissue. Moreover, a system is required that allows for easy access to the cervical vertebrae while providing accuracy in positioning the fixation screw.

Even as the cervical spine instrumentation techniques can be improved, so can the manner of fixation of the plate to the affected vertebral levels. For example, several known plates accept spinal screws at several locations, usually at the ends and in the middle of the plate. The screws may or may not be capable of being angled at varying degrees of fixation between the vertebra and the plate. In addition, some plating systems provide a locking screw which is threaded into the expansion head of the vertebral fixation screw to lock the screw into the plate. This procedure requires the installation of a separate locking screw for every fixation screw, thereby lengthening and complicating the procedure.

SUMMARY OF THE INVENTION

In an embodiment of the present invention, a method for attaching a plate to a bone is described. A guide tool having a through bore and at least one distal locating feature is provided. The distal locating feature of the guide tool is placed into a predetermined relationship with the plate. A fastener is engaged with a distal end of a driver shaft of a fastener driver. The fastener driver has a driver orientation means associated with the driver shaft. The fastener is inserted into the through bore of the guide tool with the fastener driver. The driver orientation means is mated with a guide orientation means located in the through bore of the guide tool. At least a portion of the fastener is inserted through the fastener hole. The fastener is secured into the bone through actuation of the fastener driver. At least one of a fastener travel distance, a fastener insertion orientation, and a fastener insertion pitch is guided through the mating of the driver orientation means and the guide orientation means. The fastener driver is withdrawn from the guide tool. The guide tool is withdrawn from the plate.

In an embodiment of the present invention, a system for attaching a plate to a bone is described. The plate has a fastener hole extending therethrough. A guide tool has a through bore, a guide orientation means located in the through bore, and at least one distal locating feature. The distal locating feature is adapted for placement into a predetermined relationship with the plate. A fastener driver has a driver shaft and is adapted to engage a fastener for insertion into the through bore of the guide tool. The fastener driver has a driver orientation means associated with the driver shaft. The driver orientation means is adapted for mating with the guide orientation means. At least a portion of the fastener is adapted for insertion through the fastener hole with the fastener driver. The fastener driver is actuatable to secure the fastener into the bone. At least one of a fastener travel distance, a fastener insertion orientation, and a fastener insertion pitch is guided through the mating of the driver orientation means and the guide orientation means.

In an embodiment of the present invention, a system for attaching a plate to a bone is described. The plate has a fastener hole extending therethrough. An elongated plate holder is adapted to engage the fastener hole and is manipulable to move the plate into a desired placement with respect to the bone. A guide tool has a through bore, a guide orientation means, and at least one distal locating feature. The through bore is adapted to surround at least a portion of the plate holder. The distal locating feature is being adapted for mating with at least one guide pocket extending from the fastener hole of the plate. A fastener driver has a driver shaft and is adapted to engage a fastener for insertion into the through bore of the guide tool when the plate holder has been removed from the through bore. The fastener driver has a driver orientation means associated with the driver shaft. The driver orientation means is adapted for mating with the guide orientation means. At least a portion of the fastener is adapted for insertion through the fastener hole with the fastener driver. The fastener driver is actuatable to secure the fastener into the bone.

BRIEF DESCRIPTION OF THE DRAWINGS

For a better understanding of the invention, reference may be made to the accompanying drawings, in which:

FIG. 1 is a top perspective view of a use environment for any embodiment of the present invention;

FIG. 2C is a side perspective view of the installation tool of FIG. 2A;

FIG. 2D is a side perspective view of area "2D" of FIG. 2C;

FIG. 2E is a side view of the installation tool of FIG. 2A;

FIG. 2F is a cross-sectional view taken along line "2F-2F" of FIG. 2E;

FIG. 4 is a top perspective view of a fastener;

FIG. 5A is a bottom perspective view of an installation tool of the first embodiment of the present invention;

FIG. 5B is a bottom perspective view of area "5B" of FIG. 5A;

FIGS. 6-10 depict at least a portion of a sequence of operation of the first embodiment of the present invention;

DESCRIPTION OF EMBODIMENTS

Figure 2A:
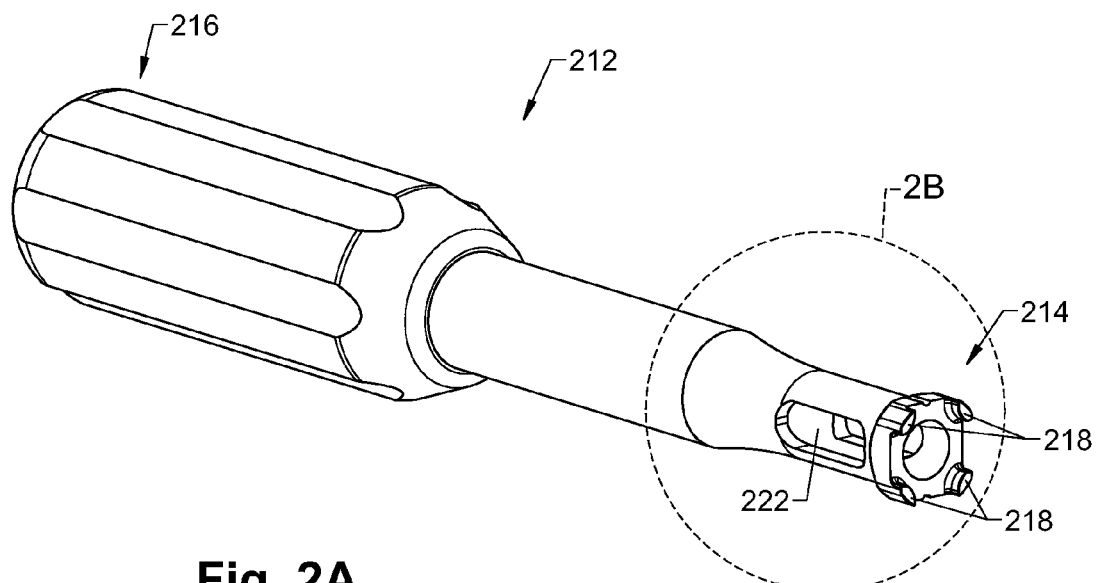
FIG. 2A is a bottom perspective view of an installation tool of a first embodiment of the present invention.
Figure 2B:
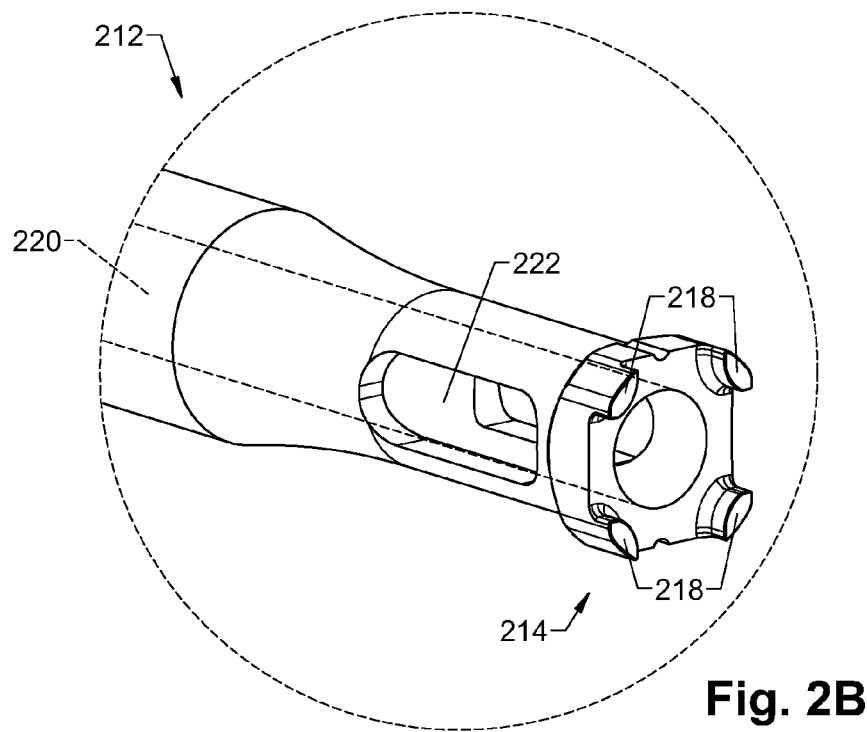
FIG. 2B is a bottom perspective view of area "2B" of FIG. 2A.

In accordance with the present invention, FIG. 1 depicts a plate 100 being attached to at least one bone 102. Here, the schematically drawn bones 102 will be shown and described as a series of vertebrae, but the present invention could be used anywhere in a patient's body, for fusing together adjacent bones, repairing a broken bone, or for any other desired purpose. The plate 100 includes at least one fastener hole 104 (three shown). Each fastener hole 104 extends from a proximal face 106 of the plate 100 and through a plate body 108 to a distal face 110 of the plate. The distal face 110 is hidden in this view, but is indicated by the dashed leader line and is located adjacent the bones 102.

FIGS. 2A-2F, 3A-3B, and 5A-5B depict various installation tools which collectively comprise a system for quickly and accurately attaching the plate 100 to the bone 102 while avoiding damage to adjacent tissues and structures, according to a first embodiment of the present invention. The tools shown and described herein may be used in any order, and may be made in any suitable manner and of any suitable materials.

FIGS. 2A-2F show various views of a guide tool 212, which may be a tubular guide tool as shown or have any other suitable dimensions or cross-sectional shape. The guide tool 212 has a distal end 214 opposite a proximal handle 216. The distal end 214 has at least one lobe 218 adapted for contact with the plate 100, as will be described below. A through bore 220 extends completely through the guide tool 212, between the proximal handle 216 and the distal end 214. The through bore 220 may be a central bore as shown or have any other suitable dimensions or cross-sectional shape. At least one view opening 222 may be provided near the distal end to facilitate visualization of the plate 100 and nearby structures and/or access thereto. As is particularly visible in the cross-sectional view of FIG. 2F, a guide orientation means 224 may be located in the through bore 220. Though the guide orientation means 224 is located within the proximal handle 216, any other suitable location of the guide orientation means may be present.

Figures 3A, 3B:
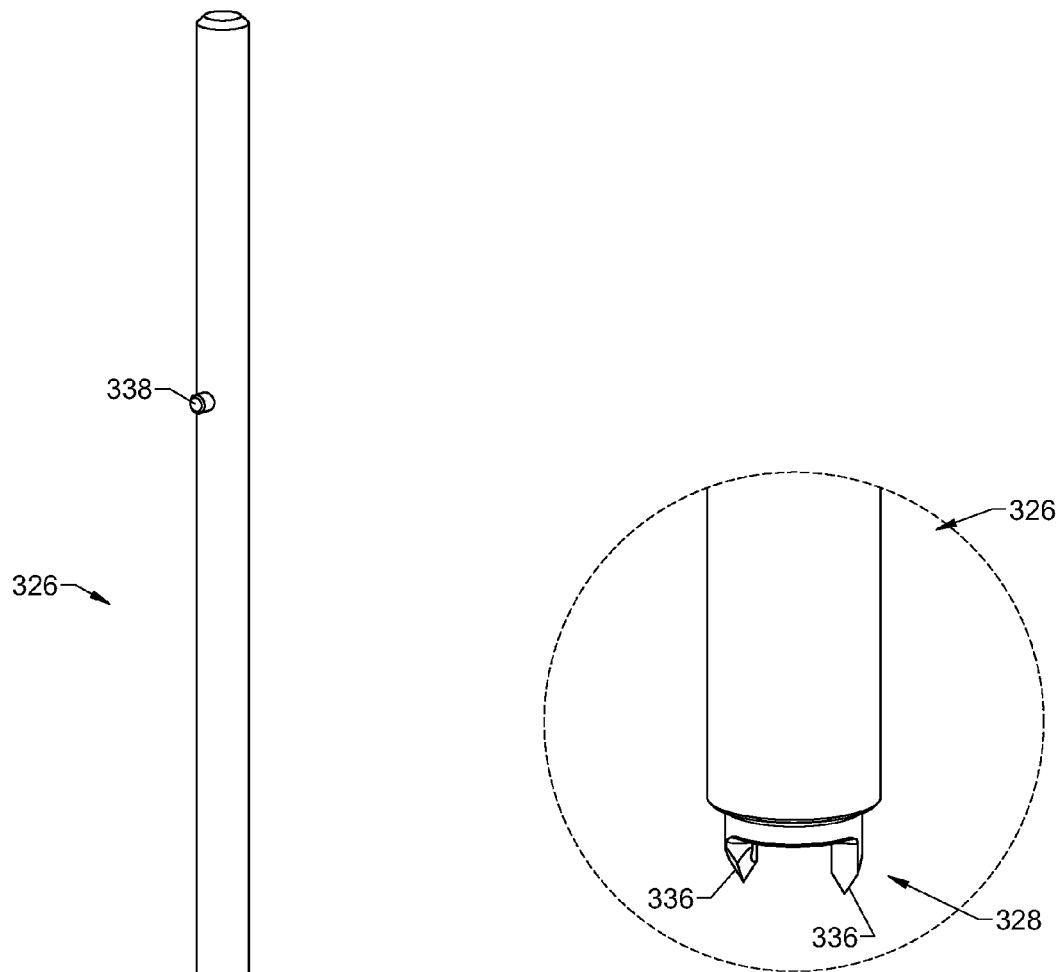
FIG. 3A is a side perspective view of an installation tool of the first embodiment of the present invention.
FIG. 3B is a side perspective view of area "3B" of FIG. 3A.

FIGS. 3A and 3B show various views of an elongated piloting member 326 having a distal end 328 adapted to prepare the bone 102 for the fastener 430, shown in FIG. 4. The fastener 430 includes a plurality of helical spikes 432 (two shown in FIG. 4) to engage the bone 102, with each helical spike 432 ending in a bone-penetrating tip 434. The elongated piloting member 326 of FIGS. 3A and 3B therefore is provided with two pilot tips 336, with each pilot tip corresponding to a bone-penetrating tip 434 of a helical spike 432 of the fastener 430. Accordingly, the pilot tips 336 can be brought into contact with the bone 102 to prepare the bone for insertion of the fastener 430. When the fastener 430 includes another style of shaft (not shown), such as the threaded post of a traditional screw or bolt, the pilot tip 336 of the corresponding piloting member 326 can readily be selected by one of ordinary skill in the art to appropriately prepare the bone 102 for insertion of the fastener having that particular style of shaft. The piloting member 326 may include a piloting orientation means 338, such as the stud-type structure shown in FIG. 3A.

FIGS. 5A and 5B show various views of a fastener driver 540 having a distal end 542, a proximal handle 544, and a driver shaft 546 extending therebetween. A driver orientation means 548, shown here as a stud-type protrusion, is associated with the driver shaft 546. The fastener 430 may be selectively engaged with the distal end 542 of the driver shaft 546 of the fastener driver 540. For example, and as shown in FIGS. 5A and 5B, one or more engagement studs 550 may be located on the distal end 542 of the fastener driver 540. These engagement studs 550 may be each adapted to frictionally engage (e.g., press-fit or wedge-fit) with a fastener drive recess feature (452, in FIG. 4). When the engagement studs 550 and fastener drive recess feature 452 are engaged, the fastener driver 540 holds the fastener 430 in a manipulable manner, and the fastener driver may be used to move the fastener to a desired location.

Operation of the first embodiment of the present invention will now be described with specific reference to FIGS. 6-10. First, and as shown in FIG. 6, the plate 100 is placed in a desired contacting relationship with the bone 102 in any suitable manner. The guide tool 212 is positioned for use, optionally with the distal locating feature (lobe 218) placed into a predetermined relationship with the plate 100. The distal locating feature 218 may contact the plate 100 when in the predetermined relationship or may be in a non-contacting arrangement; the predetermined relationship may be chosen to place the guide tool 212 in a particular orientation with respect to the plate 100, for reasons that will shortly become apparent. The guide tool 212 may grasp the plate 100 and/or the bone 102, or the guide tool 212 may simply be held by the user in the desired position. The through bore 220 may be located collinearly with a fastener hole 104. The guide orientation means 224 should be placed in a desired relationship to the plate 100, for reasons which will shortly become apparent.

Figure 7A:
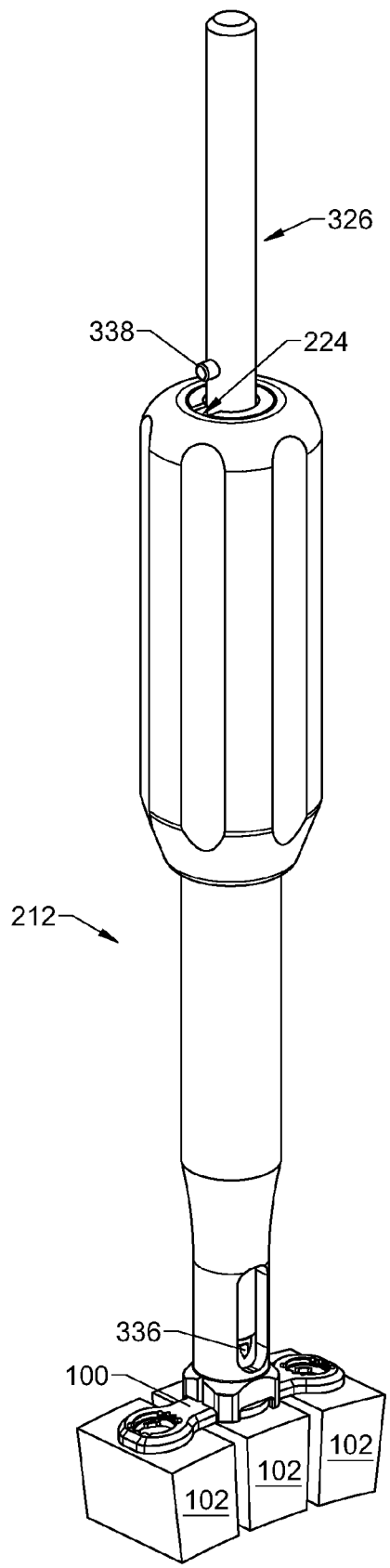
Figure 7B:
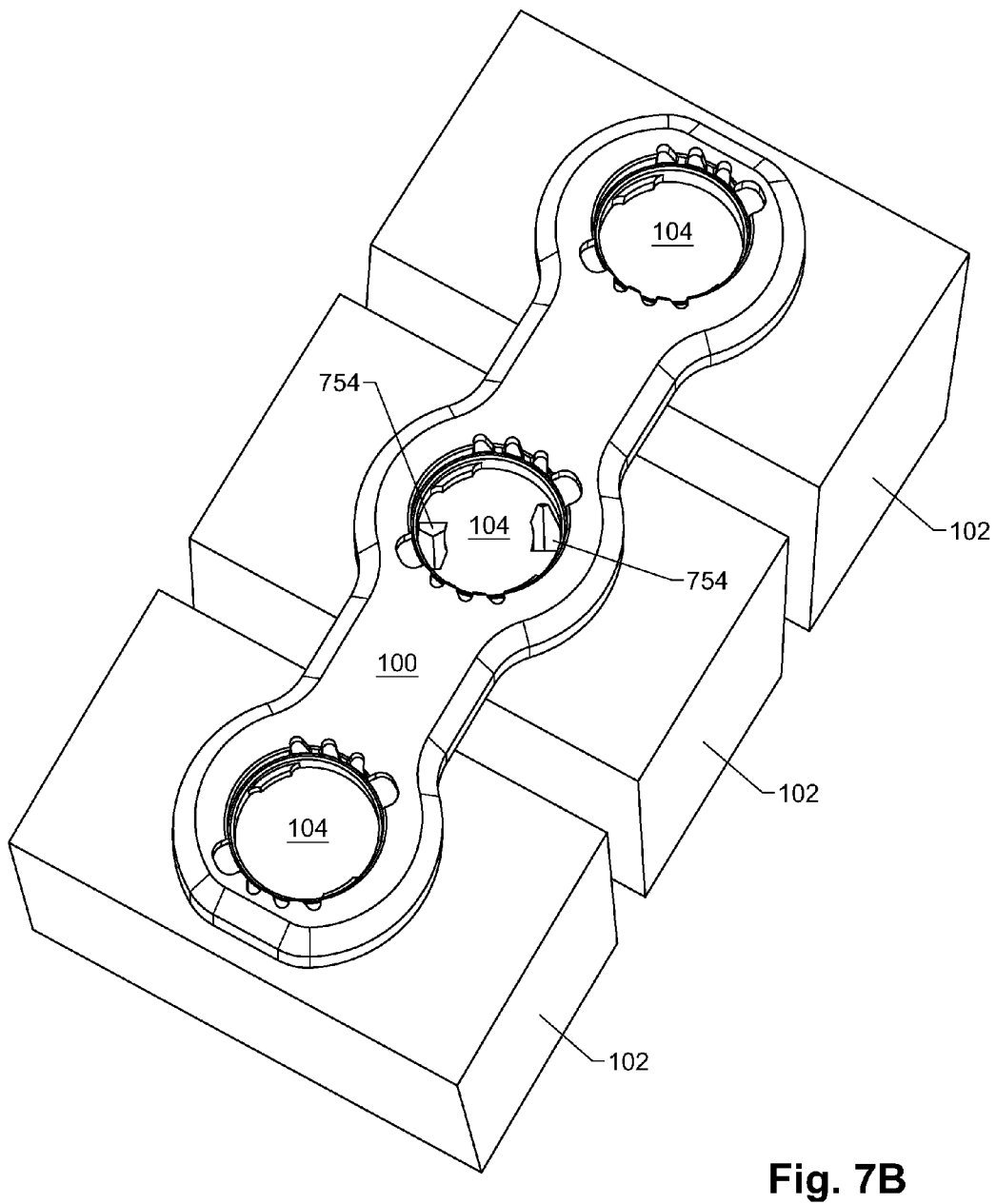

In FIG. 7A, the piloting member 326 has been inserted into the through bore 220 of the guide tool 212. Optionally, the piloting orientation means 338 may be positioned for interaction with the guide orientation means 224 to help place the pilot tips 336 substantially into the eventual insertion position of the bone-penetrating tips 434 of the fastener 430, similarly to the operation of the driver orientation means 548, set forth below. Regardless of the way that the orientation of the pilot tips 336 is determined, force may be applied to the piloting member 326 (e.g., by a downward mallet tap) to indent the bone 102 with the pilot tips 336. FIG. 7B shows the plate 100 and bone 102 after the bone has been engaged by the piloting member 326 for creation of pilot holes 754, with the guide tool 212 and piloting member having been removed from this Figure for visualization purposes.

Figure 8A:
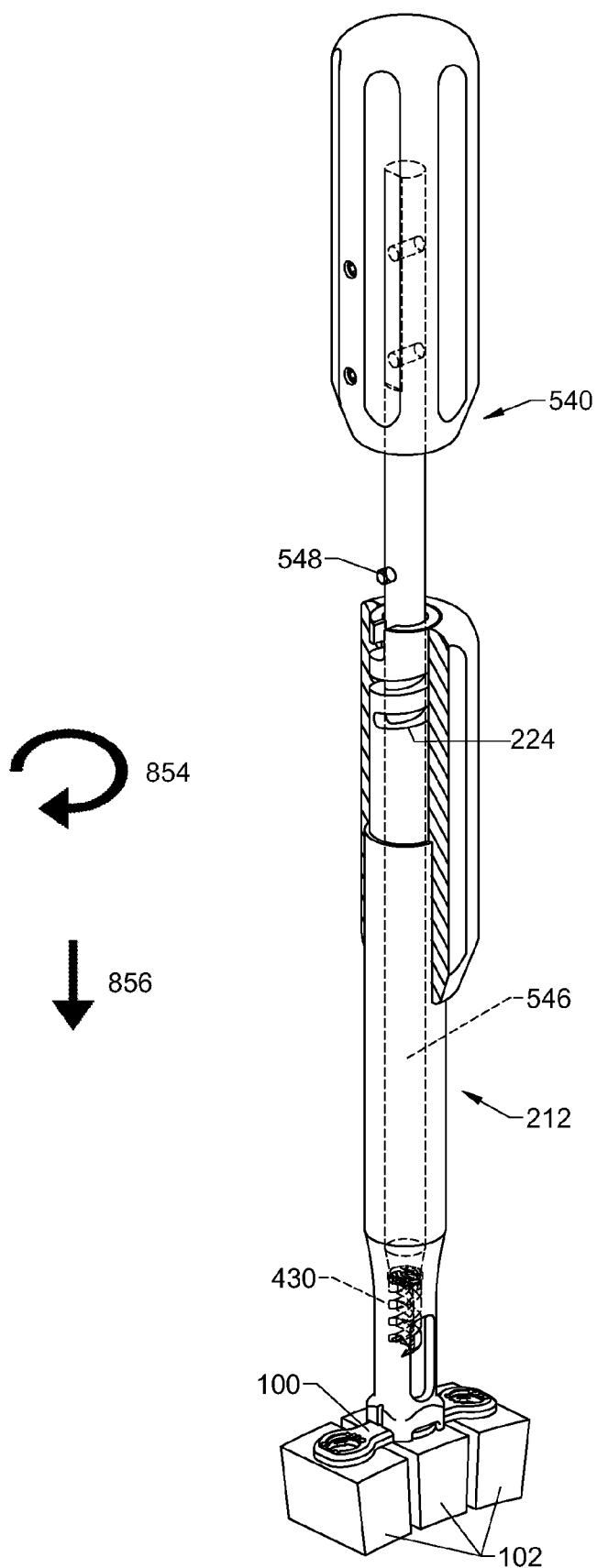
Figure 8B:
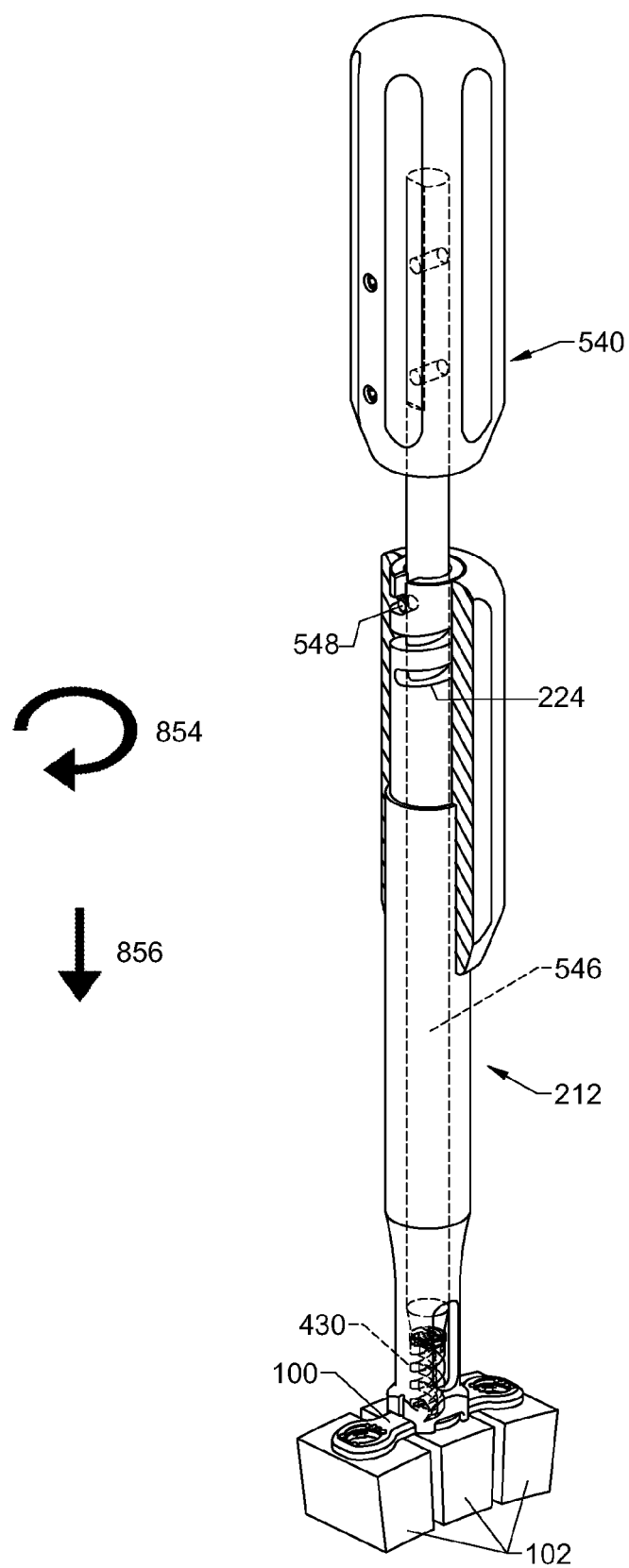
Figure 8C:
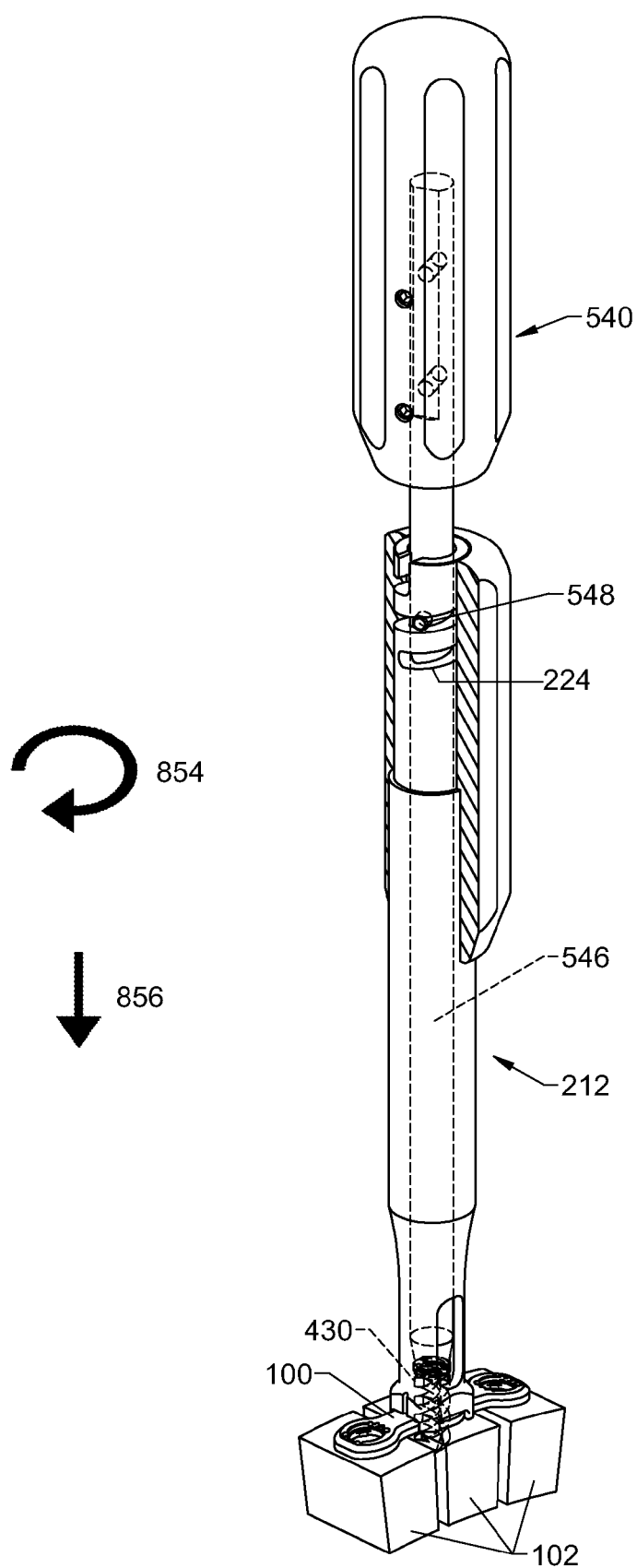
Figure 8D:
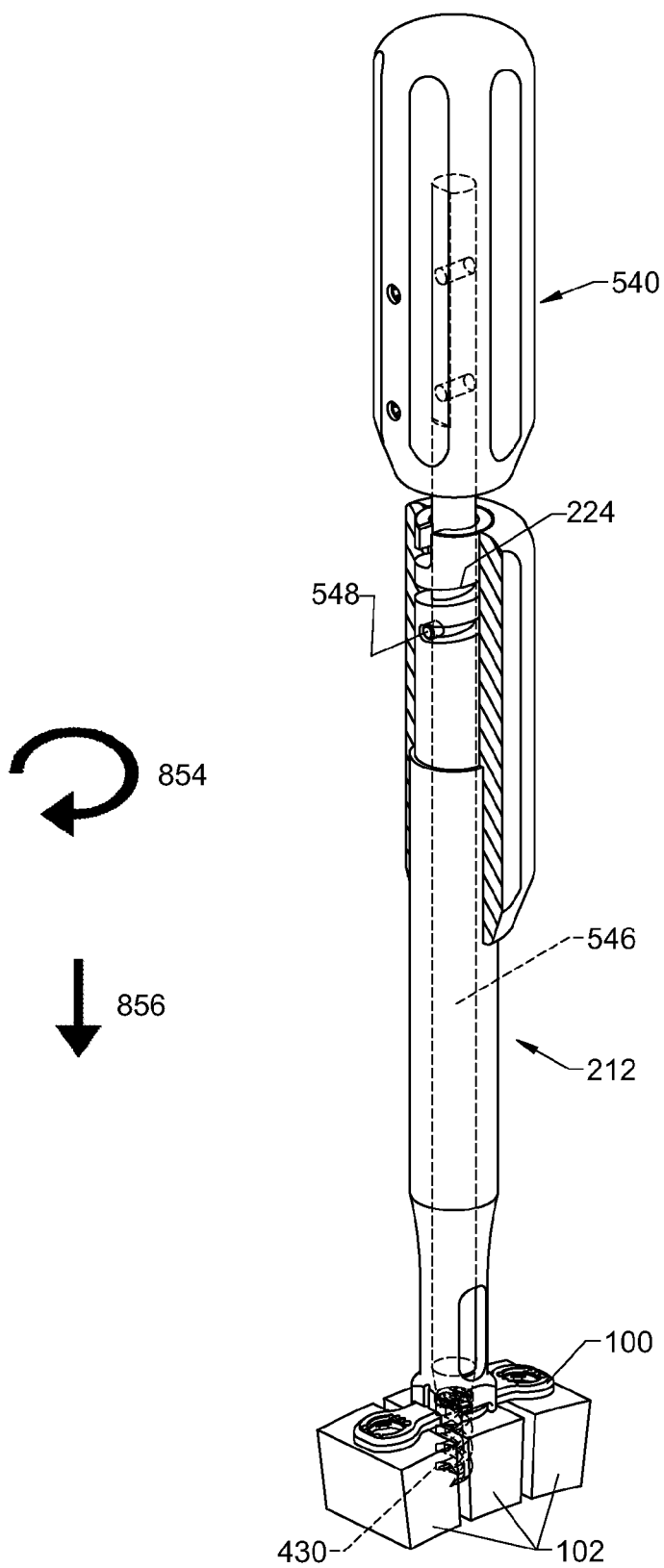

In actuality, as the surgical procedure continues, the fastener 430 will be secured into the bone 102 as shown in the sequence of FIGS. 8A-8D. In FIG. 8A, the fastener 430 has been engaged by the fastener driver 540 and inserted into the through bore 220 of the guide tool 212. The guide tool 212 is shown in partial cutaway view in FIGS. 8A-8D, to emphasize the relationship of the guide orientation means 224 and the driver orientation means 548. In FIG. 8A, the driver orientation means 548 has not yet been mated with the guide orientation means 224. The user rotates the fastener driver 540 (e.g., in the direction of clockwise arrow 854) until the driver orientation means 548 is longitudinally aligned with the proximal end of the guide orientation means 224, as shown in FIG. 8A. The user then moves the fastener driver 540 in the direction of the downward arrow 856 to mate the driver orientation means 548 and the guide orientation means 224, as shown in FIG. 8B. The driver orientation means 548 and the guide orientation means 224 are positioned on their respective fastener driver 540 and guide tool 212 to guide the fastener 430 into a desired orientation and relationship with the plate. This intentional alignment may be useful, for example, when the fastener 430 and/or the plate 100 include antibackout provisions (as discussed below), which generally need to be aligned and oriented in a particular relationship.

As the fastener driver 540 is turned clockwise 854 with downward 856 force, the fastener 430 is driven through the plate 100 and into the bone 102. During this screw driving motion, shown graphically in FIGS. 8B-8D, the mating of the driver orientation means 548 and the guide orientation means 224 guides at least one of a fastener travel distance, a fastener insertion orientation, and a fastener insertion pitch.

Figure 9:
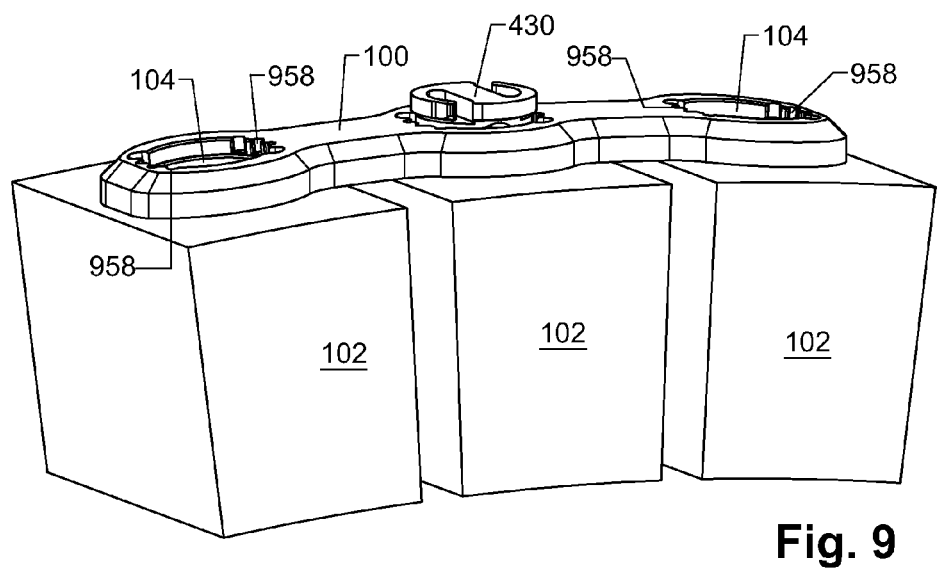
Figure 10:
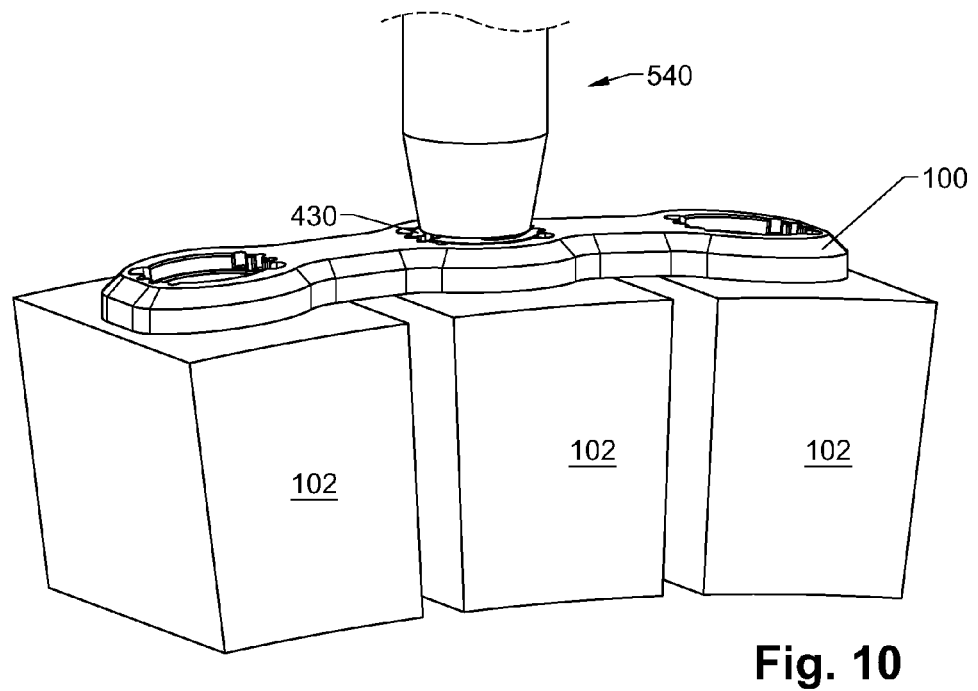

This mating of the driver orientation means 548 and the guide orientation means 224 may be helpful to the user in several ways. First, the mating of the driver orientation means 548 and the guide orientation means 224 helps in inserting the fastener 430 into the bone 102 at the desired pitch. This can be an issue, especially in soft bone 102, where, if the user applies too little or too much downward 856 force during insertion, the fastener 540 can advance too slowly or too rapidly relative to the screw pitch, and this can damage and weaken the bone and possibly decrease the holding power of the fastener 430 in the bone. Second, the distal most point of engagement (when provided) of the driver orientation means 548 and the guide orientation means 224 (shown here as a pin and helical track, respectively) acts as a hard stop, thereby limiting the depth of travel of the fastener 430 into the bone 102. This allows one or more of the fasteners 430 in a multi-fastener plate 100 to be inserted less than completely into the bone 102, as shown in FIG. 9. At such a partially-inserted stage, when utilized, the fasteners 430 are able to hold the plate 100 in place on the bone 102, but any provided antibackout feature between the fastener 430 and the plate 100 has not yet begun to engage. For example, a fastener anti-backout feature 453 may be a cantilevered pawl, as shown, and the plate 100 may include one or more plate anti-backout features 958, such as the serrations shown, which engage with the fastener anti-backout feature 453 in a ratcheting manner. When the fastener 430 is not totally secured within the bone 102, the user can confirm that the plate 100 is correctly positioned on the bone. When the fastener and plate antibackout features 453 and 958 have not yet been engaged, the plate 100 can be easily removed and repositioned, if desired. If the plate 100 position is acceptable, the user can then use the fastener driver 540 without the guide tool 212 to finish securing the fastener(s) 430, as shown in FIG. 10. Final tightening of the fastener 430 engages the fastener and plate antibackout features 453 and 958 and secures the fastener to the plate 100.

The ratcheting relationship of the fastener antibackout feature 453 and the plate antibackout feature 958 helps to provide at least one discrete rotational position between the plate 100 and a fully secured/installed fastener 430. In order to achieve a desired relative ending position for the fastener antibackout feature 453 and the plate antibackout feature 958, one of ordinary skill in the art can readily design and orient the guide orientation means 224 and driver orientation means 548 accordingly. This may be desirable, for example, when a fastener hole 104 includes one or more lugs (160 in FIG. 1) which protrude radially inward into the fastener holes. These lugs 160, when present, may be located within the gaps in between the helical spikes 432 of the fastener 430 while the fastener is being driven into the bone 102. The guidance provided by the mating of the driver orientation means 548 and the guide orientation means 224 helps to cause the fastener 430 to enter the fastener hole 104 with the lugs 160 positioned as desired within the gaps between the helical spikes 432.

FIGS. 11A-14 depict various installation tools which collectively comprise a system for quickly and accurately attaching the plate 100 to the bone 102 while avoiding damage to adjacent tissues and structures, according to a second embodiment of the present invention. The tools shown and described herein may be used in any order, and may be made in any suitable manner and of any suitable materials. Elements of FIGS. 11A-14 which are similar to those of FIGS. 1-10 are indicated by the same number with the addition of a prime. Description of structure and function of elements of the second embodiment which is substantially similar to the description above with reference to the first embodiment is omitted below, for brevity.

Figures 11A, 11B, 11C:
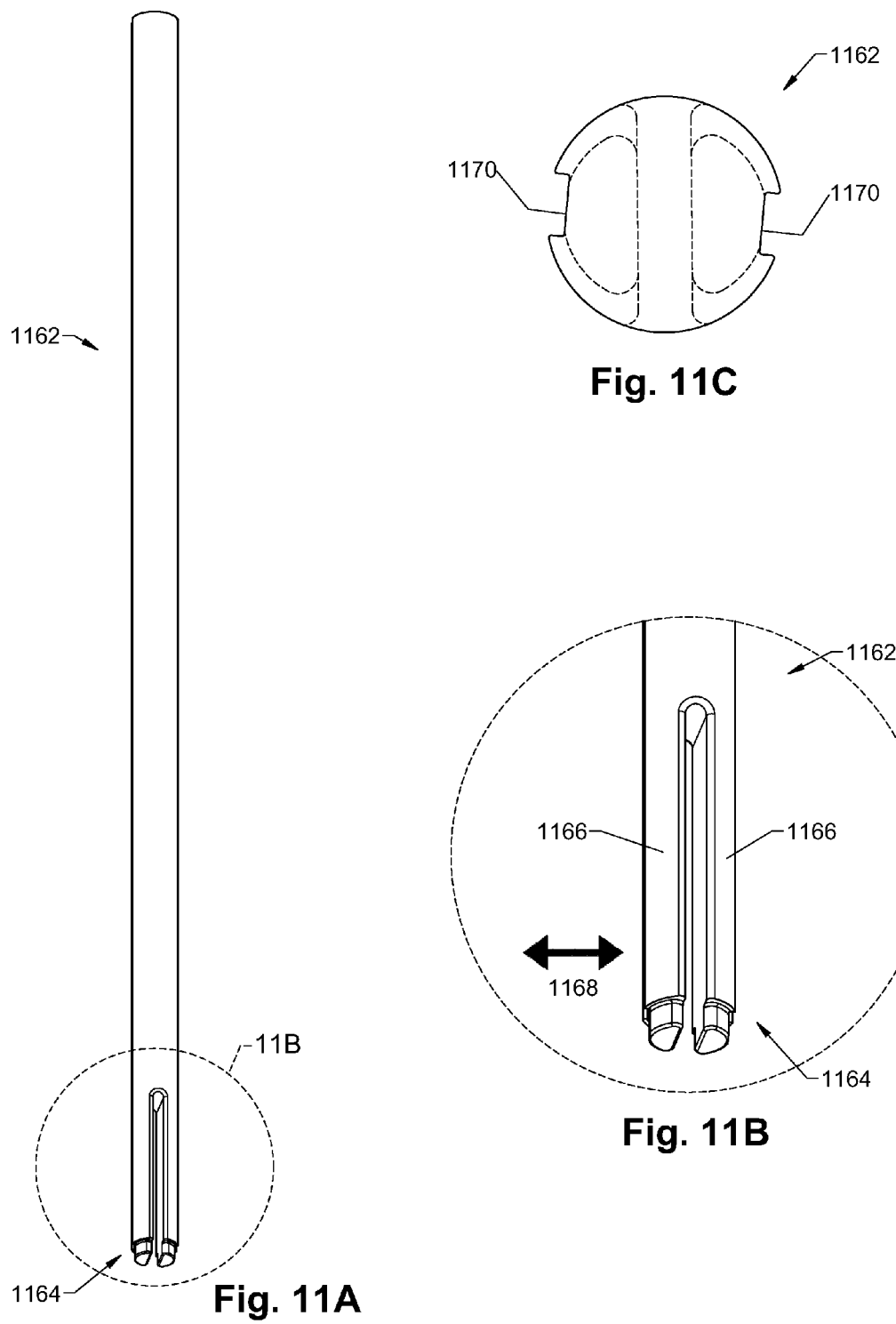
FIG. 11A is a bottom perspective view of an installation tool of a second embodiment of the present invention.
FIG. 11B is a bottom perspective view of area "11B" of FIG. 11A.
FIG. 11C is a top view of the installation tool of FIG. 11A.

FIGS. 11A-11C show various views of an elongated plate holder 1162 having a distal end 1164 which includes at least two spring force legs 1166. The spring force legs 1166 may be tapered at the distal end 1164, as shown. No portion of the plate holder 1162 should exceed an inner diameter size of the through bore 220' of the guide tool 212'. The spring force legs 1166 may be adapted to resist an inward force exerted in the lateral direction 1168, either through the use of a resistance mechanism (not shown) or simply through a stiff resilience of the material making up the plate holder 1162. The plate holder 1162 includes at least one side channel 1170 which is positioned and configured to help guide a guide tool 212' into a desired relationship with a fastener hole 104', as discussed below.

Figure 12A:
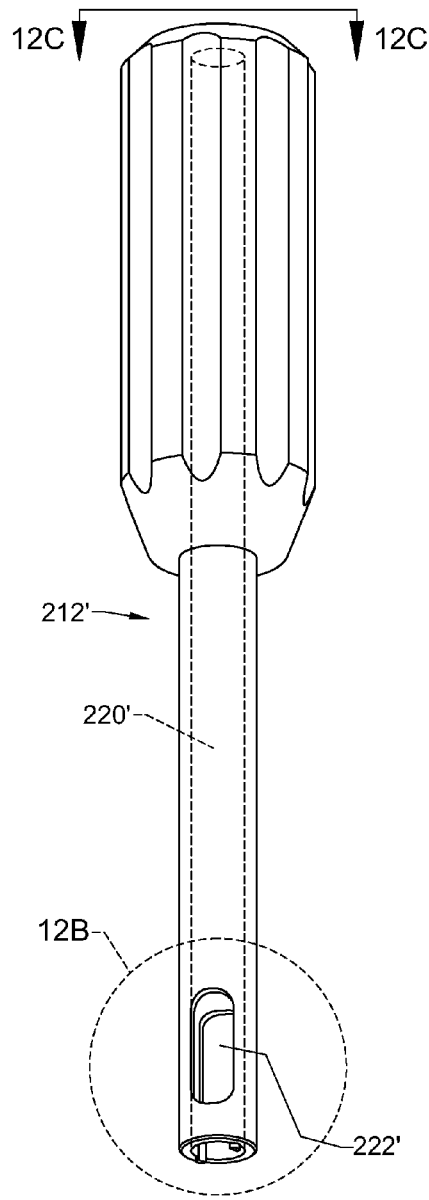
FIG. 12A is a side perspective view of an installation tool of the second embodiment of the present invention.
Figure 12B:
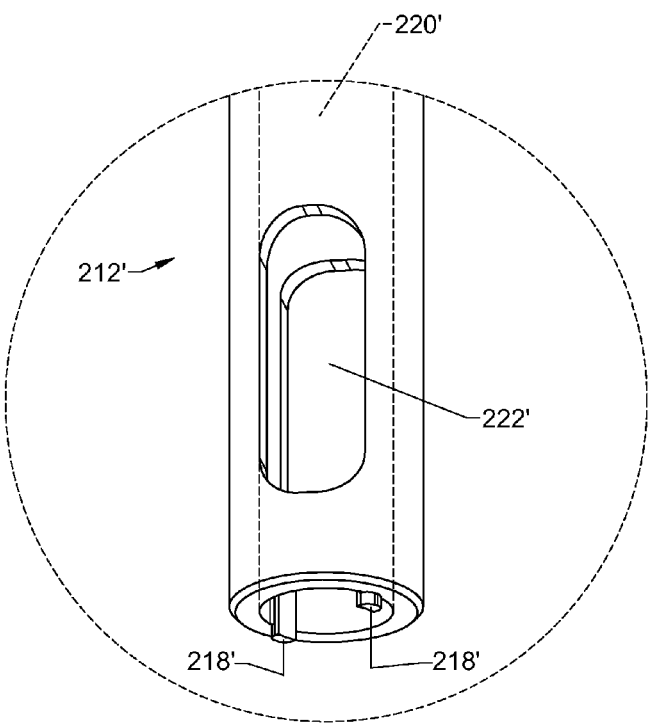
FIG. 12B is a bottom perspective view of area "12B" of FIG. 12A.
Figure 12C:
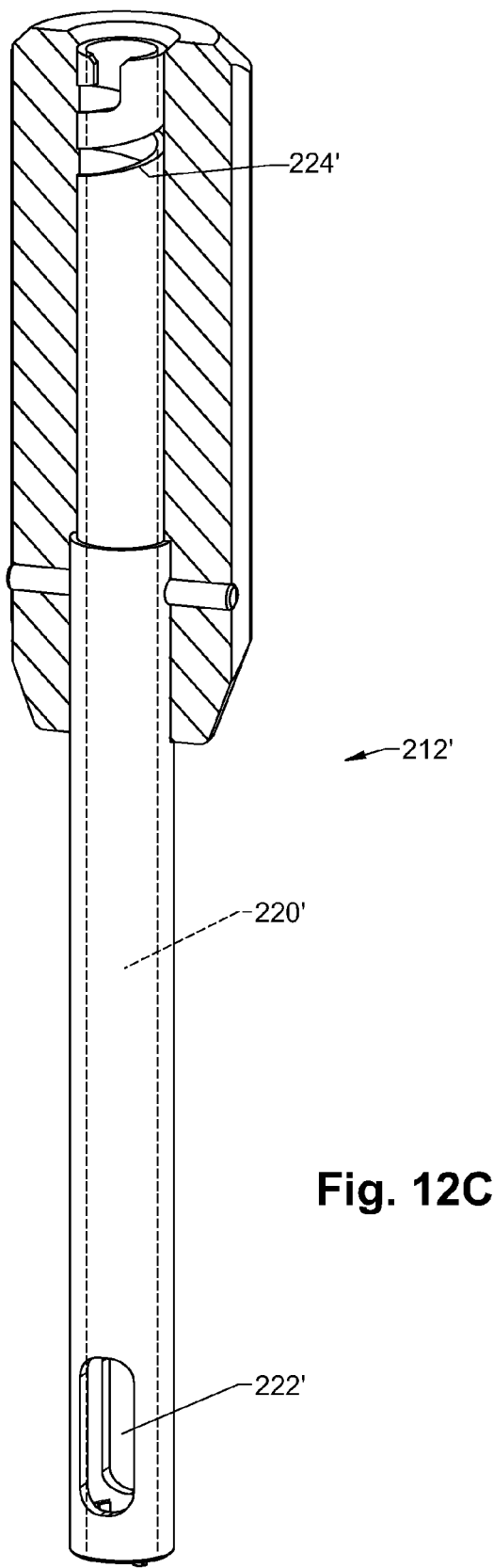
FIG. 12C is a partial cross-sectional view taken along line "12C-12C" of FIG. 12A.

FIGS. 12A-12C show various views of a guide tool 212' for use with the second embodiment of the present invention. The lobes 218' of the guide tool 212' protrude from the through bore 220' and are constructed more compactly with the guide tool 212' of the second embodiment than are the lobes 218 of the guide tool 212 of the first embodiment, for reasons which will become apparent shortly.

Figure 13A:
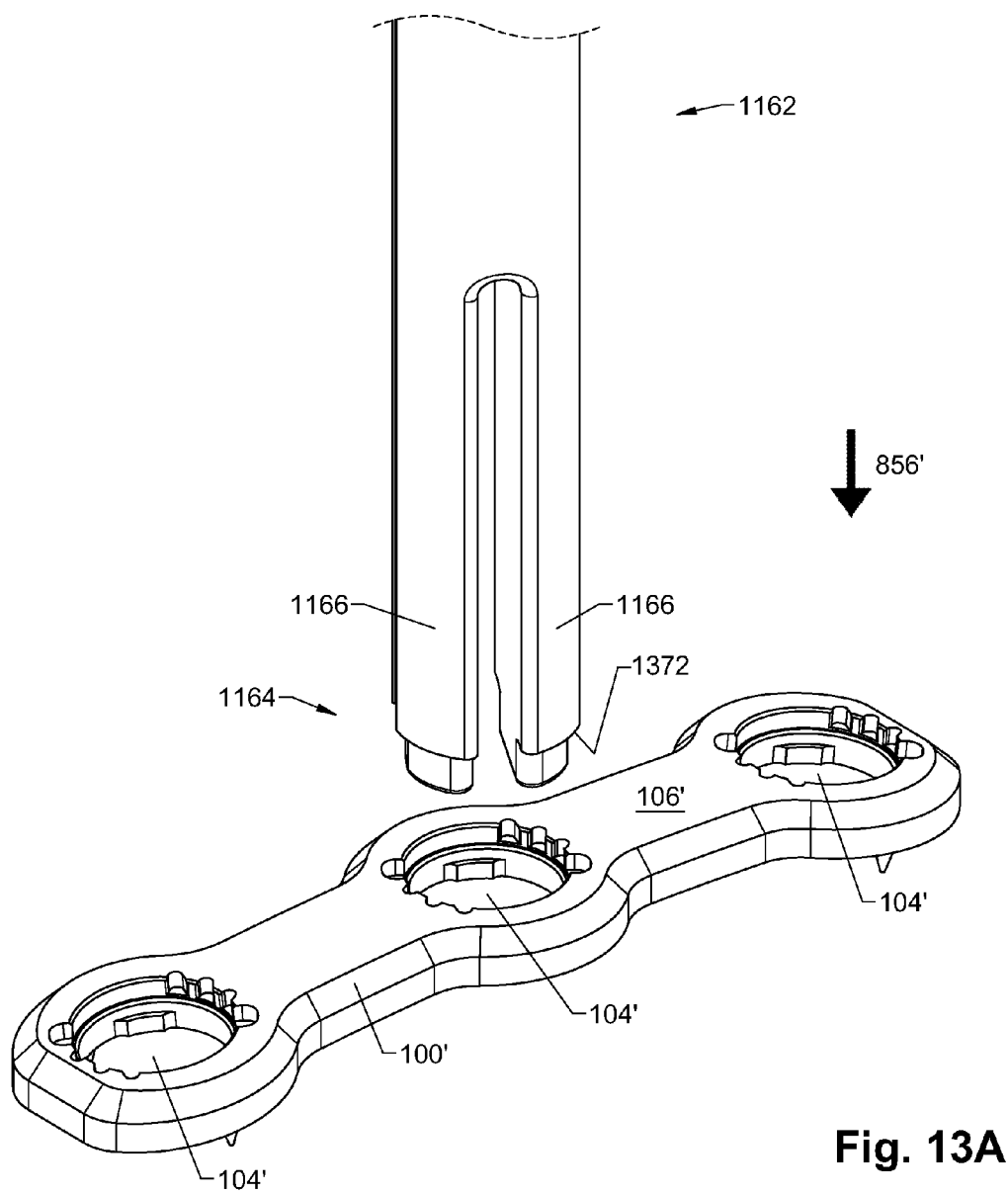
FIGS. 13A-C depict at least a portion of a sequence of operation of the second embodiment of the present invention.
Figure 13B:
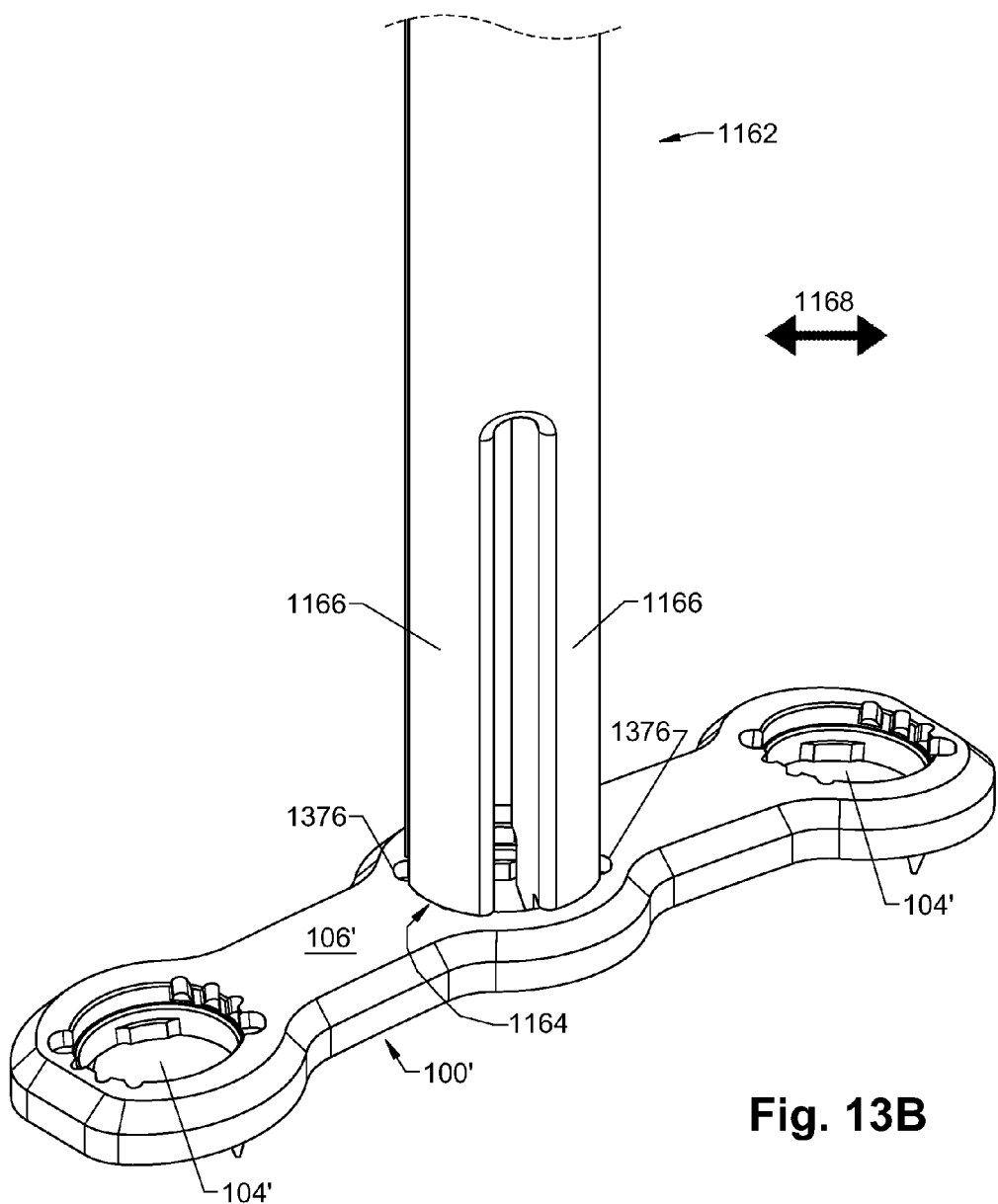
Figure 13C:
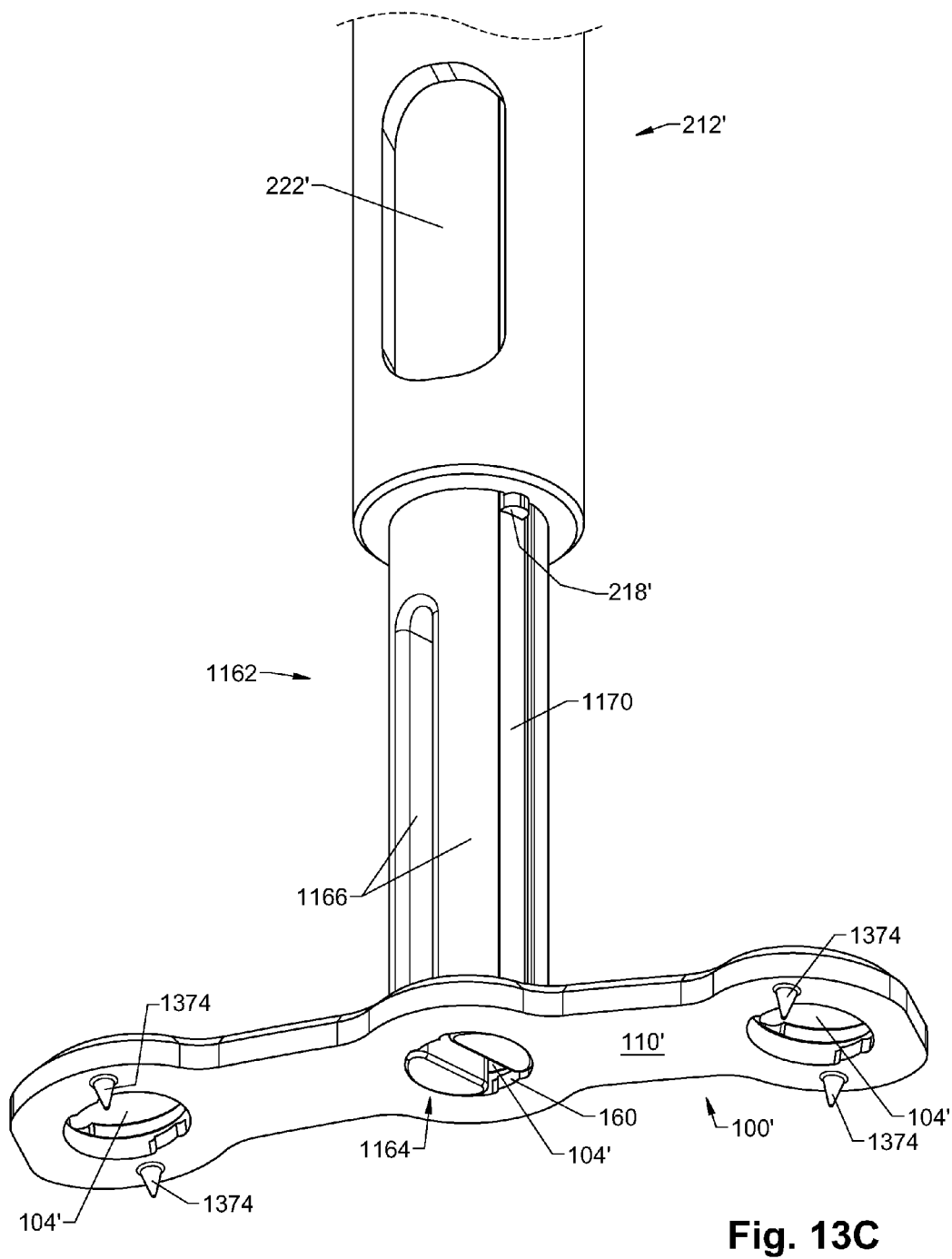
Figure 14:
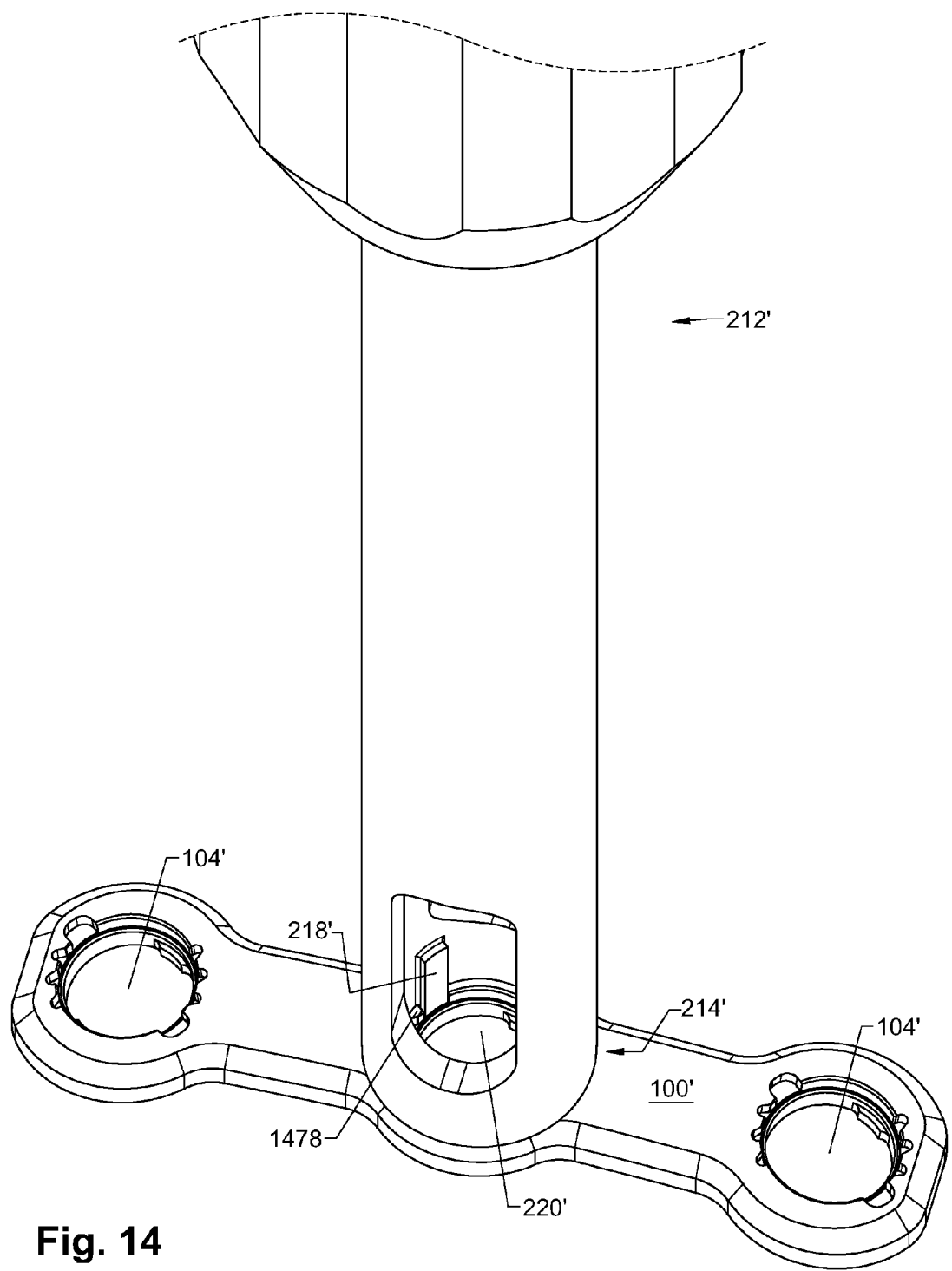
FIG. 14 depicts at least a portion of the sequence of operation of the second embodiment of the present invention.

FIGS. 13A-14 depict selected steps in the operation of the second embodiment of the present invention. In the sequence of FIGS. 13A-13B, the distal end 1164 of the plate holder 1162 is inserted in the fastener hole 104' for engagement thereof. For example, the total diameter of the distal end 1164 of the plate holder 1162 may be slightly larger than the inner diameter of the fastener hole 104', thus introducing frictional engagement via a force exerted upon the fastener hole by the plate holder in the lateral direction 1168. As another example, a spring expansion mechanism (not shown) could be located within the distal end 1164 of the plate holder. Because of the engagement, however provided, the plate holder 1162 grasps the plate 100' and may be manipulated to move the plate into a desired placement with respect to the bone 102'.

Also in FIGS. 13A and 13B, an optional shoulder 1372 may be seen. The shoulder 1372, when present, interacts with the proximal face 106' of the plate to prevent the inserted distal end 1164 of the plate holder 1162 from extending or protruding beyond the distal face 110' of the plate 100', which can be seen in FIG. 13C. The distal end 1164 of the plate holder 1162 can accordingly be flush with, or slightly retracted proximally into, the plate 100' and thus not exert a downwardly 856' directed force upon the bone 102'.

Also in FIG. 13C, a plurality of retaining pins 1374 may be seen to protrude from the distal face 110' of the plate 100'. When present, the retaining pins 1374 may be pressed into the bone 102' to temporarily retain the plate 100' in a desired placement with respect to the bone 102'. One example method of pressing the retaining pins 1374 into the bone 102' is to apply force to a proximal end (not shown in this view) of the plate holder 1162 to engage the bone with the retaining pins.

FIG. 13C shows the lugs 160' of the plate 100' as being located in the unnumbered gap laterally between the spring force legs 1166 when the spring force legs are inserted into the fastener hole 104'. The lugs 160' may substantially prevent the spring force legs 1166 from rotary movement within the fastener hole 104'.

Also in FIG. 13C, the relationship of the lobes 218' of the guide tool 212' to the side channels 1170 of the plate holder 1162 is shown. The side channels 1170 accept and guide the lobes 218' as the guide tool 212' is slid downward 856' around the plate holder 1162. Each side channel 1170 may extend at least semi-contiguously with a guide pocket 1376, where each guide pocket 1376 extends from the fastener hole 104' of the plate 100'. The guide pockets 1376 are thus operative to orient the guide tool 212' into a particular rotary relationship with the fastener hole 104'. Accordingly, one of ordinary skill in the art could readily design one or more of the lobe(s) 218', side channel(s) 1170, guide pocket(s) 1376, spring force leg(s) 1166, lug(s) 160', or any other distal locating feature(s) or other structures of the present invention to place the guide tool 212' in a desired orientation with respect to the fastener hole 104', and as a result, the guide orientation means 224' (in a known location on the guide tool 212') can readily be placed to mate with the driver orientation means 548' to guide the fastener 430' into a substantially precise final installation position.

Optionally, and as shown in FIG. 14, the lobe 218' may include at least a portion protruding into the through bore 220' of the guide tool 212'. Also as shown in FIG. 14, this internally-oriented lobe 218' may be positioned to interact with a ratchet tooth 1478 of the plate antibackout feature 958', in order to help restrict rotation of the guide tool 212' with respect to the fastener hole 104'. It should be noted that, regardless of the structures located permanently or temporarily within the through bore 220', the through bore should generally allow a free clearance inside diameter equal to or greater than the effective inside diameter (usable space) within the fastener hole 104'. In this manner, any items which need to enter and/or pass through the fastener hole 104' can fit through the through bore 220'. An example of an exception to this recommendation, however, might be one or more protruding lugs (not shown) within the through bore 220' which are oriented and placed to remain within the gap between the helical spikes 432' of the fastener 430' as the fastener is screwed into engagement with the bone 102—such lugs may function to reduce the free clearance inside diameter, yet be present for the purpose of helping to orient and/or guide the helical spikes. Other examples of possible obstructions to the free clearance inside diameter recommendation above are the guide, piloting, and/or driver orientation means 224', 338', and 548', as such may need to interact with the guide tool 212', piloting member 326', and/or fastener driver 540 to provide a desired "stop" function to the system of the present invention.

FIG. 14 shows the guide tool 212' after the plate holder 1162 has been withdrawn in a proximal direction from the through bore 220'. The guide tool 212' is now ready to accept and guide the fastener driver 540' and fastener 430' to secure the plate 100' to the bone 102' with the fastener in a manner similar to that set forth above with reference to the first embodiment of the present invention.

It is contemplated that the guide orientation means 224 and driver orientation means 548 of any embodiment of the present invention may have any suitable form, placement, size, orientation, interaction, or any other physical characteristics. For example, either one of the driver orientation means 548 and the guide orientation means 224 may protrude from its respective fastener driver 548 and guide tool 212, while the other of the driver orientation means and the guide orientation means may be recessed into its respective fastener driver and guide tool. At least one of the driver orientation means 548 and the guide orientation means 224 may include an internal thread having the same pitch as the fastener 430, with the other of the driver orientation means and the guide orientation means having a corresponding external thread. Either of the driver orientation means 548 and the guide orientation means 224 may be located at any suitable interior or exterior location on its respective fastener driver 540 and guide tool 212. Similar options and configurations may be readily provided by one of ordinary skill in the art for the lugs 160' and spring force legs 1166, and the side channels 1170 and lobes 218'.

Various embodiments of the present invention, whether or not explicitly described and shown herein, may include a wide range of differing and similar features, structures, and functions. One of ordinary skill in the art can readily choose any of these or any other features, structures, and/or functions in constructing alternate embodiments of the present invention, without regard as to whether that particular combination of features, structures, and/or functions was described as a separate embodiment herein.

While aspects of the present invention have been particularly shown and described with reference to the preferred embodiments above, it will be understood by those of ordinary skill in the art that various additional embodiments may be contemplated without departing from the spirit and scope of the present invention. For example, at least one of the guide orientation means 224 and driver orientation means 548, the fastener driver 540 and fastener 430, or any other structures of the system may be placed into a magnetic relationship with each other. The clockwise description of fastener driver 540 operation is based upon a common mechanical screw-engagement standard; a ratcheting feature, counter-clockwise engagement, or even longitudinal impact-driving motion, as well as any other desired driving motion, could be additionally or alternatively provided. The plate holder 1162 may grasp the plate differently than shown; for example, an adhesive structure, frangible linkage, turn-lock mechanism, or any other suitable grasping means may be controllable by the user to grasp and release the plate 100'. At least one lobe 218 and plate 100, or guide pocket 1376 and lobe 218', could be dimensioned for frictional engagement to allow the plate 100, 100' to be manipulated by the guide tool 212, 212'. Any of the actions making up the described sequences of operation may be performed in any order, concurrently and/or serially. A structure described herein as "contacting" another structure could also or instead engage that other structure in any suitable manner. Any structures of the present invention can permanently or temporarily frictionally engage any other structure(s) as desired, using any suitably designed static or dynamic components to do so. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, we claim:

1. A system for attaching a plate to a bone, the system comprising:
   a plate having at least one fastener hole extending from a proximal face of the plate and through a plate body to a distal face of the plate;
   a fastener;
   a guide tool having a through bore defining a longitudinal axis therethrough, a guide orientation means located in the through bore, and at least one distal locating feature, the distal locating feature being selectively placed in a predetermined contacting relationship with the plate to place the guide tool in a particular orientation with respect to the plate;
   a fastener driver having a driver shaft and being adapted to engage the fastener for insertion into the through bore of the guide tool, the fastener driver having a driver orientation means associated with the driver shaft, the driver orientation means being a stud-type protrusion adapted for mating with the guide orientation means; and
   an elongated plate holder having a distal end adapted for insertion and frictional engagement with the fastener hole, the plate holder being manipulable to move the plate into a desired placement with respect to the bone, and wherein the plate holder is adapted for at least partial insertion into the through bore of the guide tool;
   wherein at least a portion of the fastener is inserted through the fastener hole with the fastener driver, the fastener driver being actuatable to secure the fastener into the bone;
   wherein the distal locating feature remains in contact with the plate during at least a portion of the insertion of the fastener into the bone; and
   wherein a predetermined fastener rotational insertion orientation with respect to the longitudinal axis of the guide tool is guided through the mating of the stud-type protrusion and the guide orientation means when the guide tool has achieved the particular orientation with respect to the plate via placement of the distal locating feature in the predetermined contacting relationship with the plate.

* * * * *